United States Patent [19]

Frankel et al.

[11] Patent Number: 4,555,957

[45] Date of Patent: Dec. 3, 1985

[54] BI-DIRECTIONAL LIQUID SAMPLE HANDLING SYSTEM

[75] Inventors: Arthur E. Frankel, Palo Alto; Larry J. Johnson, San Jose; Timothy J. Wennberg, San Francisco, all of Calif.

[73] Assignee: Cetus Corporation, Emeryville, Calif.

[21] Appl. No.: 542,113

[22] Filed: Oct. 14, 1983

[51] Int. Cl.$^4$ ............................................. G01N 35/06
[52] U.S. Cl. ............................... 73/864.14; 73/864.16; 73/864.25
[58] Field of Search ........... 73/863.32, 864.16, 864.24, 73/864.25; 422/100

[56] References Cited

U.S. PATENT DOCUMENTS

| | | |
|---|---|---|
| 3,143,393 | 8/1964 | De Seguin Des Hons . |
| 3,687,632 | 8/1972 | Natelson ........................... 73/864.25 |
| 3,772,154 | 11/1973 | Isenberg et al. . |
| 3,831,618 | 8/1974 | Liston . |
| 3,912,456 | 10/1975 | Young ............................... 73/864.25 |
| 4,036,381 | 7/1977 | Nielsen . |
| 4,076,503 | 2/1978 | Atwood et al. . |
| 4,106,911 | 8/1978 | Marcelli . |
| 4,265,855 | 5/1981 | Mandle et al. . |
| 4,299,796 | 11/1981 | Esch . |
| 4,340,390 | 7/1982 | Collins . |
| 4,451,433 | 5/1984 | Yamashita . |
| 4,478,094 | 10/1984 | Salomaa ........................... 73/863.32 |

FOREIGN PATENT DOCUMENTS

| | | |
|---|---|---|
| 042337 | 12/1981 | European Pat. Off. . |
| 052006 | 5/1982 | European Pat. Off. . |
| 2123593 | 9/1972 | France . |
| 2323184 | 4/1977 | France . |
| 2446480 | 8/1980 | France . |
| 52-69383 | 9/1977 | Japan . |

Primary Examiner—S. Clement Swisher
Attorney, Agent, or Firm—Albert P. Halluin; Janet E. Hasak; Thomas E. Ciotti

[57] ABSTRACT

An automatic liquid transfer system includes a horizontally translatable table and a pipette that is translatable both vertically and horizontally in a direction transverse to the axis of translation of the table. The table accommodates one or more titer trays having a multiplicity of receptacles to be filled, or holding liquid samples to be diluted, transferred, or aspirated, and a rack housing plural rows of disposable tips. Between each cycle in a liquid transfer process, a fresh tip is picked up by the pipette and used to transfer liquid in a sterile manner from a sample or diluent source to a well in the titer tray, or from one well to a different well anywhere on the one tray or to a receptacle in a different tray, where it is mixed with diluent. Thereafter, the tip is discharged back into the rack to maintain sterile conditions during the process and a new tip is installed.

11 Claims, 5 Drawing Figures

BI-DIRECTIONAL LIQUID SAMPLE HANDLING SYSTEM

BACKGROUND OF THE INVENTION

The present invention is directed to an apparatus for performing automatic transfer of liquid samples between a plurality of receptacles. More specifically, it is directed to a system for transferring liquid samples between a multiplicity of separate liquid receptacles, such as is required, for example, in serial dilution and chemical analysis of liquid samples in microtiter trays where each receptacle holds only about one tenth to ten milliliters of liquid. A serial dilution operation basically involves mixing a sample with successively increasing proportions of a diluent in separate receptacles to obtain a series of successively decreasing concentrations of the sample. The various sample concentrations can then be assayed to determine a particular property. For example, the sample might be a serum and the assay might be used to determine which concentration of the serum provides optimum results when reacted with a particular substance.

Initially, assay of a sample was performed manually, wherein different reagents would be mixed in different respective test tubes, for example with the aid of a syringe or pipette. This procedure consumed a considerable amount of time when a number of different assays were required. Consequently, machines for automatically or semi-automatically performing assays were developed. One example of such a machine is disclosed in commonly assigned U.S. Pat. No. 4,478,094.

OBJECT AND BRIEF STATEMENT OF THE INVENTION

The machine disclosed in that patent is sound in both structure and operation, and it is desired to improve upon certain aspects thereof. More particularly, it is an object of the present invention to provide an added degree of versatility to the machine disclosed in the aforementioned patent by enabling the liquid dispensing and transferring pipette head to move both vertically and horizontally transverse relative to longitudinal horizontal movement of the receptacle tray. This provides three dimension movement between the pipette head and any given well in one or more microtitre trays or liquid in one or more supply troughs carried by the table. With this added freedom of movement, liquid transfers are not constrained within the individual rows of receptacles in the microtiter trays. Rather, liquid can be transferred from a receptacle in one row to a receptacle in a different row, as well as between different receptacles in the same row or to any given receptacle in a different tray. Thus, a greater variety of liquid combinations and concentrations can be obtained in the receptacles of the tray.

These and other features of the present invention are discussed in greater detail hereinafter with reference to a preferred embodiment thereof illustrated in the accompanying drawings.

DETAILED DESCRIPTION

Figure 1:
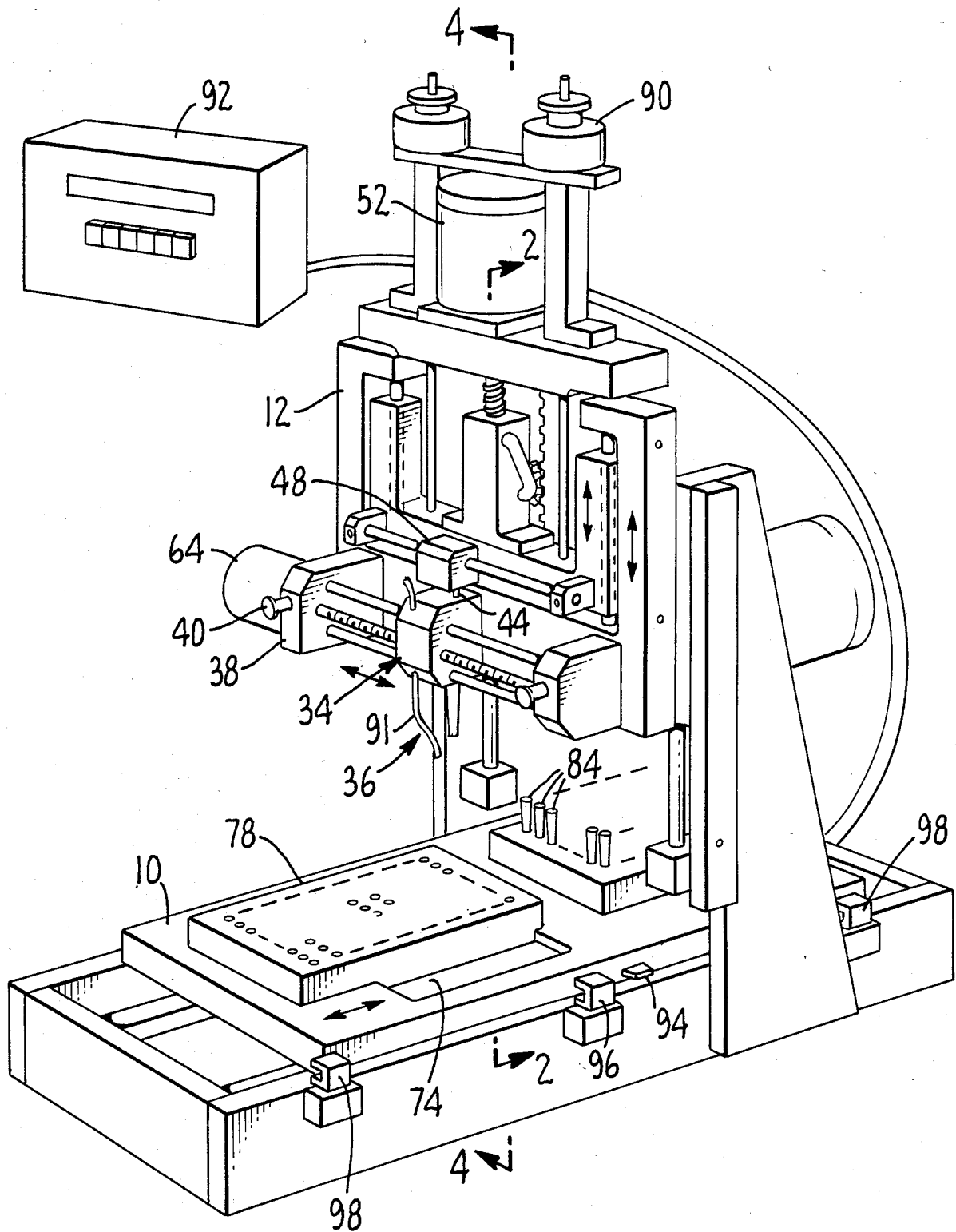
FIG. 1 is a perspective view of a liquid transfer machine implementing the features of the present invention.
Figure 4:
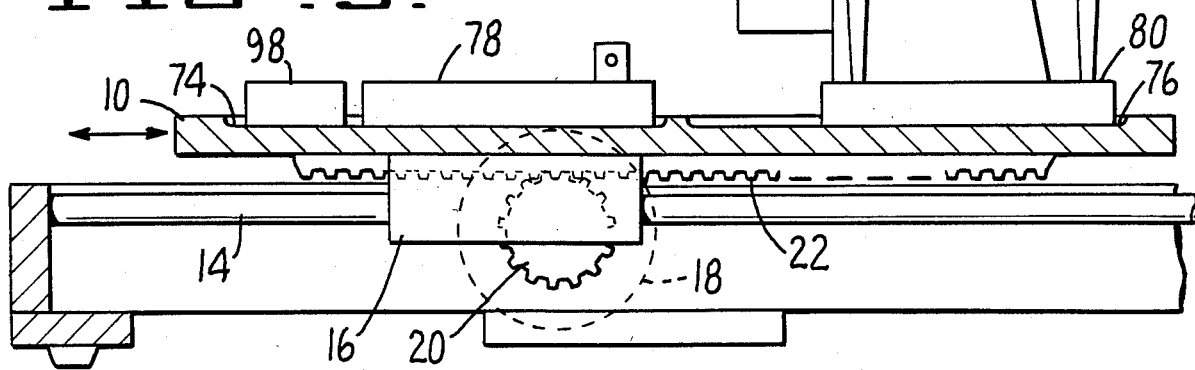
FIG. 4 is a sectional side view of the liquid transfer machine, taken along the section line 4—4 of FIG. 1.

Referring to FIG. 1, an automatic liquid transfer machine includes two principal moving components, a horizontally translatable table 10 and a vertically translatable head assembly 12. As best illustrated in FIG. 4, the table 10 is mounted for horizontal translation on hardened guide rods 14 by means of slide bearings 16. Translation of the table is provided by a stepper motor 18 through longitudinal drive means, which may include a pinion 20 connected to the motor and a rack 22 mounted on the underside of the table. Similarly, the head 12 is mounted for vertical translation on guide rods 24 by means of slide bearings 26. Translation of the head assembly is provided by a stepper motor 28 through another longitudinal drive means, such as pinion 30 and rack 32.

The head assembly 12 supports a pipette assembly 34. This assembly includes a single pipette 36 that is horizontally translatable in a direction transverse to the axis of translation of the table 10. The pipette is removably attached to the head assembly by means of mounting blocks 38 and connecting pins 40, and moves vertically therewith. A plunger mechanism 42 is mounted on the head assembly for vertical movement relative to the pipette. The plunger mechanism includes a plunger rod 44 disposed within the pipette 36. The rod is connected to an actuator bar 46 by means of a slide block 48. The bar 46 is vertically translated along guide rods 50 by means of a stepper motor 52 and lead screw mechanism 54.

Figure 3:
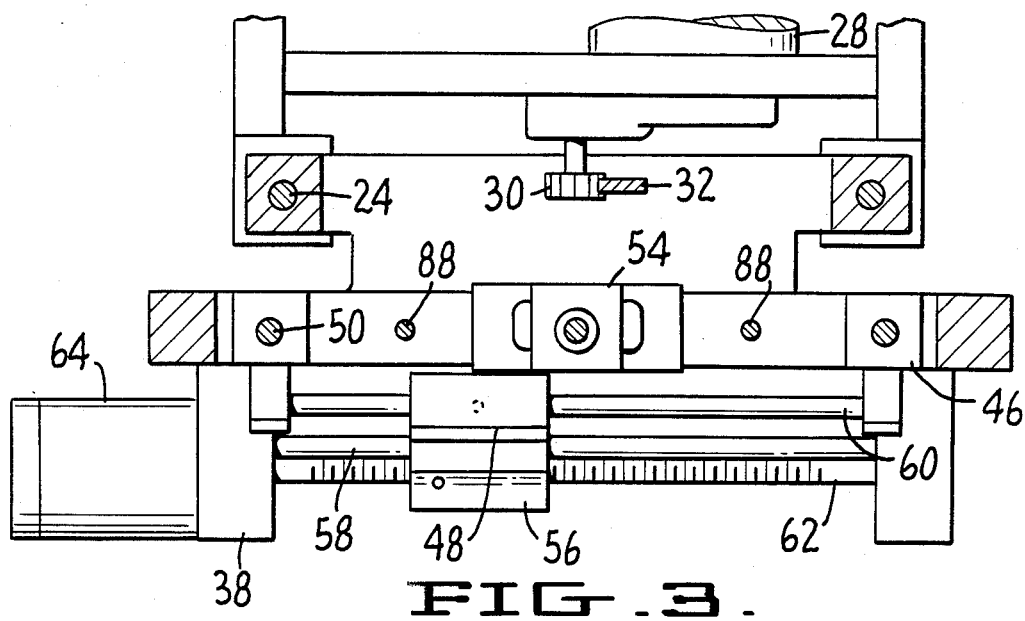
FIG. 3 is a sectional top view of the liquid transfer machine.
Figure 2:
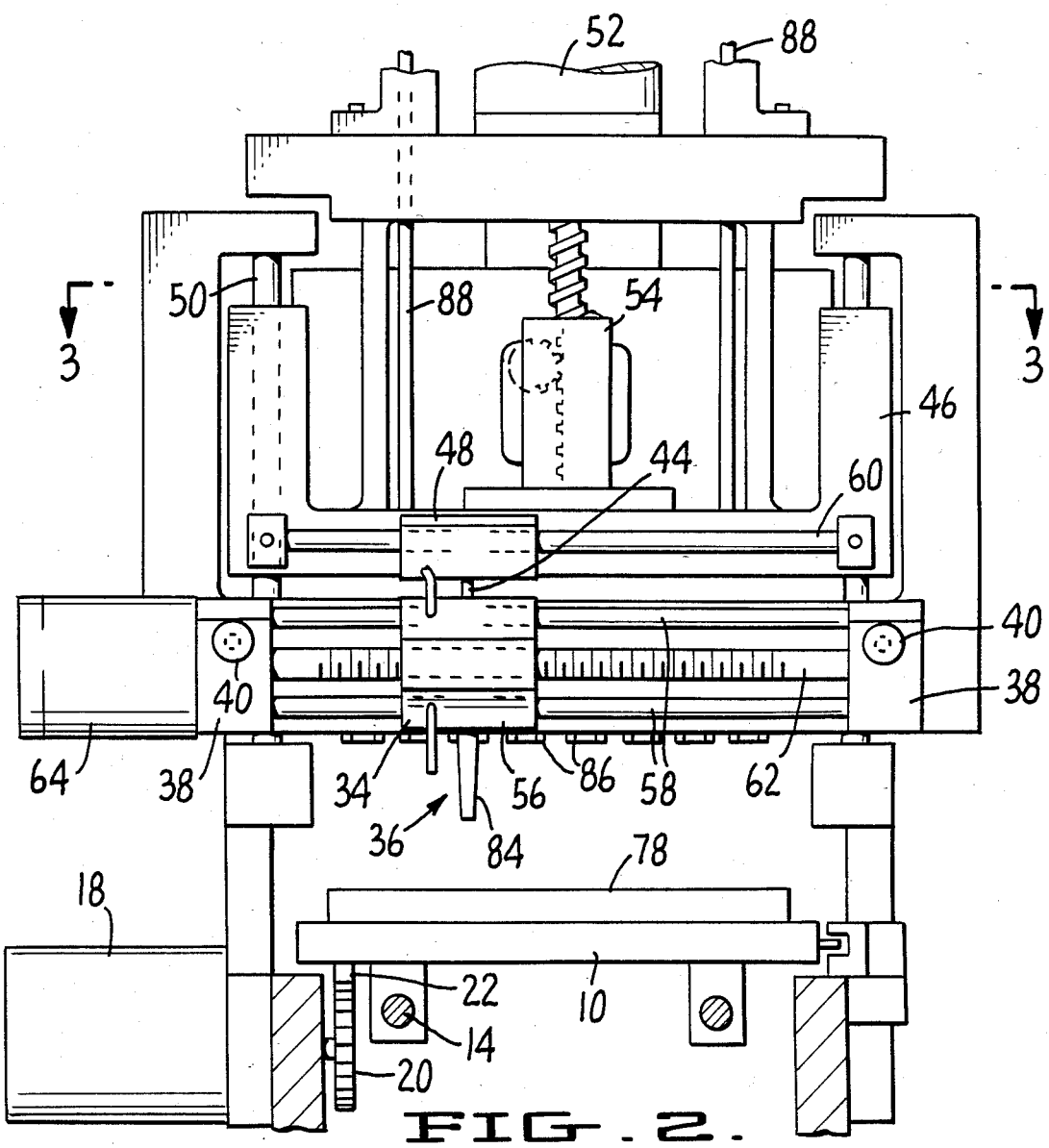
FIG. 2 is a sectional front view of the liquid transfer machine taken along the section line 2—2 of FIG. 1.

The added versatility which is afforded by the present invention arises from the fact that the pipette assembly 34, in addition to moving vertically with the head 12, can move horizontally in a direction transverse to the axis of translation of the table 10. Referring to FIGS. 2 and 3, a support block 56 is disposed for horizontal translation along a pair of guide rods 58 mounted between the mounting blocks 38. Similarly, the slide block 48 on which the plunger rod 44 is mounted can translate along a guide rod 60 attached to the actuator bar 46.

The horizontal translation of the support block 56, and hence the pipette 36 mounted thereon, is effected by means of a lead screw 62 driven by a stepper motor 64. This motor can be supported on one of the mounting blocks 38. The slide block 48, which is connected to the support block 56 by the plunger rod 44, follows the horizontal translation of the support block.

Figure 5:
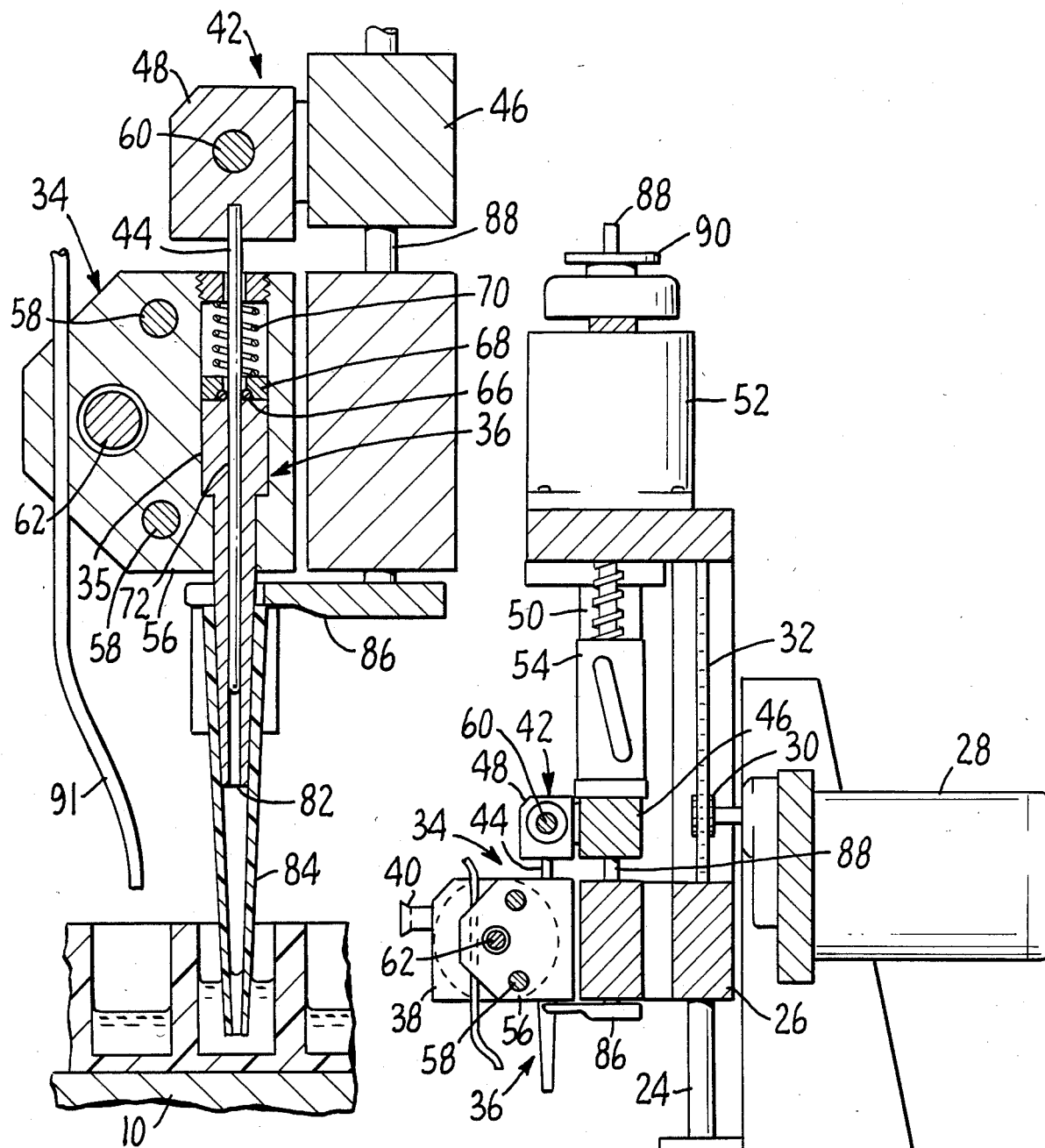
FIG. 5 is an enlarged, sectional side view of the pipette assembly.

As best illustrated in the detailed sectional diagram of FIG. 5, vertical translation of the plunger rod 44 relative to the pipette nozzle section 35 changes the internal air volume of the bore of the pipette nozzle, causing fluid to be aspirated into or expelled. An air tight seal is provided between the rod and the top of the pipette nozzle by means of a seal ring 66, held by a grommet 68 and a compliance spring 70. The pipette nozzle 35 forms a piston section 72 which is reciprocable in a cylinder formed in the support block 56. Pipette nozzle 35 is thereby restrained vertically by the spring 70 so that during a tip loading step, pipette nozzle 35 can slide vertically in the block 56 against the compliance spring 70. This allows nose portion 82 of pipette nozzle 35 to reliably pick up tips of slightly different dimensions and to assure that the open ends of the tips are at the same elevation relative to the table 10 and a titer tray mounted thereon.

The table 10 includes two work stations 74 and 76 for respectively accommodating two trays. One of the trays can be a conventional titer tray 78 that includes a matrix arrangement of wells for housing liquid samples. The other tray 80 at the rear work station 76 can be a tip tray that contains a similar arrangement of receptacles that accommodate disposable pipette tips. A typical titer tray might contain 96 wells in a 12×8 matrix pattern. Preferably, the tray 78 can be accommodated at the forward work station 74 in a transverse orientation, or in the longitudinal direction of the table 10.

Referring again to the detailed side view of FIG. 5, the bottom or nose end 82 of each pipette nozzle 35 is tapered or otherwise formed on its exterior surface so as to receive and frictionally engage the inner surface of a disposable pipette tip 84. Such frictional engagement is to form an air tight seal therebetween. A tip 84 in a row of receptacles in the tip tray 80 is inserted onto and engages the end of the pipette 36 when the head assembly 12 is lowered by the stepper motor 28 after the table 10 has brought one row of tips 84 into registry with the pipette. The walls of the receptacles in the tip tray 80 are arranged to center the tips 84 for engagement with the tapered end 82 of the pipette 36.

The subsequent removal of the tip 84 from the pipette is accomplished with a tip ejector. The tip ejector includes a bar 86 that is disposed between the support block 56 and the upper shoulder of the tip 84. The bar 86 is connected to and supported by a pair of vertically translatable rods 88 mounted on the head assembly 12. These rods are translated by means of a pair of drive means, such as solenoids 90 mounted on the top of the head assembly. When the solenoids 90 are deactuated, the ejector bar 86 is maintained in the upper position illustrated in FIG. 5. Actuation of the solenoids moves the bar vertically downward, to push the tip 84 down and release it from its frictional engagement with the end 82 of the pipette nozzle 35. A step motor and lead screw arrangement may be used as the drive means instead of solenoids 90, if desired.

To enable the machine to be used for filling operations as well as liquid transfers, a dispensing tube 91 can be mounted on the support block 56. The end of this tube terminates at a well-defined location adjacent the end of the pipette 36. For example, it might be spaced forward of the pipette by a distance equal to the spacing between two wells in a microtiter tray. The remote end of the tube 91 is connected to a precision metering pump (not shown) which is in turn connected to a supply of reagents with which the wells are to be filled.

The operation of each of the stepper motors 18, 28, 52 and 64, as well as the solenoids 90, is controlled by a suitable microprocessor 92. Basically, the microprocessor 92 functions to control the sequence of operations of each of these elements, and thus the interrelated movements of the table 10, the head assembly 12, the pipette assembly 34 and the tip ejector bar 86 to effect transfer of liquid from one well in the tray 78 at the forward work station 74 to another well in that tray. Alternatively, a third work station can be provided on the table 10, and the transfer of liquid can occur between any well of either of two trays at the two work stations. Such a second tray 98 is indicated in FIG. 4. Since the stepper motors provide a predetermined amount of rotation in response to each actuating signal applied thereto, accurate positioning of the movable elements can be obtained, for example, through appropriate control of the number or duration of actuating pulses, or other signals supplied by the microprocessor.

In addition to controlling these various movable elements, the microprocessor 92 also monitors their movement through appropriately positioned sensors. For example, as shown in FIG. 1, a sensor arrangement for the table 10 can include a blade 94 that is attached to and extends from the side of the table, and a position sensor 96 that detects when the blade 94, and hence the table 10, passes through a predetermined reference point in its translation. Each time the table passes through this point, the position sensor 96 sends a signal to the microprocessor 92 that enables the microprocessor to update information relating to the table's position. Thus, if the stepper motor 18 should miss an actuating pulse during translation of the table, or if the pulse count stored within the microprocessor 92 should not coincide with the position of the table, the error will not be carried over to successive cycles of operation.

In addition to the reference sensor 96, a pair of limit sensors 98 can be disposed at the respective ends of the path of travel of the table. A signal sent by these sensors indicates that the table is nearing the end of its travel, and provides an indication to the microprocessor 92 to interrupt the supply of power to the stepper motor 18 or take some other such corrective action. Similar sensor arrangements can be provided to monitor the movement of the head assembly 12, the actuator bar 46 and the support block 56.

In operation, the automatic liquid transfer machine basically functions to pick up a tip in the tray 80, insert it in one of the wells in the tray 78, extract some of the liquid sample from this well, inject the tip into a reagent in another one of the wells, oscillate the plunger to mix the liquid, position the tip to expell all liquid and then return the tip to the tray 80, as disclosed in greater detail in the aforementioned application.

As mentioned previously, the instant invention provides an added degree of flexibility to this basic operation. Since the pipette is capable of moving in two perpendicular horizontal directions relative to the table 10, as well as vertically relative thereto, liquid can be transferred from any given well in the tray 78 to any other well in that tray, and even to any well or receptacle in another tray on the table.

It will be appreciated by those of ordinary skill in the art that the present invention can be embodied in other specific forms without departing from the spirit or essential characteristics thereof. The presently disclosed embodiment is therefore considered in all respects to be illustrative and not restrictive. For example, where the term "stepper" motor has been used to describe the preferred embodiment of the motor drive means for the table, head assembly and pipette assembly, it will be apparent that other precise positioning means may be used, such as direct current servo motors. The scope of the invention accordingly is indicated by the appended claims rather than the foregoing description, and all changes that come within the range of equivalence thereof are intended to be embraced therein.

What is claimed is:

1. A machine for automatically transferring at least a portion of a liquid sample in one receptacle to another receptacle, comprising:
   a head assembly translatable between upper and lower positions along a vertical axis;
   means for moving said head assembly along said vertical axis;
   at least one pipette assembly mounted on said head assembly for movement therewith along said vertical axis and for movement in a single first horizontal axis, said pipette assembly including a support block carried on a first horizontal guide member and a pipette nozzle mounted on said support block and having a depending end for receiving tips, a slide block carried on a second horizontal guide member parallel to the first guide member, a plunger mounted on said slide block and depending within said pipette nozzle, and means for moving said plunger within said pipette nozzle to vary the internal volume of said nozzle and a tip supported thereby;
   means for moving said pipette assembly relative to said head assembly along said first horizontal axis;
   a table mounted beneath said head for translation along a second horizontal axis that is transverse to the first horizontal axis, said table having at least two work stations spaced along its axis of translation for respectively accommodating at least one tray having a plurality of receptacles;
   means for moving said table along said second horizontal axis to place any selected one of said plurality of receptacles in a tray mounted on said table at either of said work stations in registry with said pipette assembly; and
   means for controlling each of said moving means for said head assembly, pipette assembly, plunger and table to effect transfer of a liquid sample between at least one receptacle in said try mounted at one of said stations to at least one receptacle located at the other of said work stations.

2. The liquid transfer machine of claim 1 further including a tip ejector mounted on said head assembly for removing a tip disposed on said depending end of said pipette nozzle, and wherein said controlling means further provides coordinated control of said tip ejector and said moving means to replace a tip on the end of said pipette with another tip disposed in a receptacle of a tray mounted at a third work station or said table between liquid transfer steps.

3. The machine of claim 2 wherein said tip ejector means includes a bar disposed adjacent at least a portion of said depending end and movable downward to push disposable tips from said end.

4. The machine of claim 3 further including at least one driven means for moving said bar downwardly.

5. The machine of claim 1 wherein said head assembly moving means includes a stepper motor and a longitudinal drive means interconnecting stepper motor and said head assembly.

6. The machine of claim 1 wherein said plunger moving means includes a stepper motor and a lead screw mechanism interconnecting said stepper motor and said plunger.

7. The machine of claim 1 wherein said table moving means includes a stepper motor and a longitudinal drive means interconnecting said stepper motor and said table.

8. The machine of claim 1 wherein said pipette assembly moving means includes a stepper motor and a lead screw interconnecting said stepper motor and said support block.

9. The machine of claim 1 wherein said control means includes means for monitoring the position of at least one element including said head assembly, pipette assembly, plunger and table.

10. The machine of claim 9 wherein said monitoring means includes a sensor producing a reference signal each time a monitored element passes a predetermined point in its path of travel.

11. The machine of claim 1 further including a dispensing tube mounted on said pipette assembly and terminating at a predetermined location relative to said depending end of said pipette.

* * * * *

REEXAMINATION CERTIFICATE (800th)
United States Patent [19]
Frankel et al.

[11] B1 4,555,957
[45] Certificate Issued Dec. 22, 1987

[54] BI-DIRECTIONAL LIQUID SAMPLE HANDLING SYSTEM

[75] Inventors: Arthur E. Frankel, Palo Alto; Larry J. Johnson, San Jose; Timothy J. Wennberg, San Francisco, all of Calif.

[73] Assignee: Cetus Corporation, Emeryville, Calif.

Reexamination Request:
No. 90/001,182, Mar. 6, 1987

Reexamination Certificate for:
Patent No.: 4,555,957
Issued: Dec. 3, 1985
Appl. No.: 542,113
Filed: Oct. 14, 1983

[51] Int. Cl.$^4$ .................................................. G01N 35/06
[52] U.S. Cl. .............................. 73/864.14; 73/864.16; 73/864.25
[58] Field of Search ............ 73/863.32, 864.16, 864.24, 73/864.25, 864.13, 864.17, 864.18; 422/100; 436/180

[56] References Cited
U.S. PATENT DOCUMENTS

| | | | |
|---|---|---|---|
| 3,687,632 | 8/1972 | Natelson | 73/864.25 |
| 3,832,135 | 8/1974 | Drozdowski et al. | 73/864.25 |

*Primary Examiner*—Stewart J. Levy

[57] ABSTRACT

An automatic liquid transfer system includes a horizontally translatable table and a pipette that is translatable both vertically and horizontally in a direction transverse to the axis of translation of the table. The table accommodates one or more titer trays having a multiplicity of receptacles to be filled, or holding liquid samples to be diluted, transferred, or aspirated, and a rack housing plural rows of disposable tips. Between each cycle in a liquid transfer process, a fresh tip is picked up by the pipette and used to transfer liquid in a sterile manner from a sample or diluent source to a well in the titer tray, or from one well to a different well anywhere on the one tray or to a receptacle in a different tray, where it is mixed with diluent. Thereafter, the tip is discharged back into the rack to maintain sterile conditions during the process and a new tip is installed.

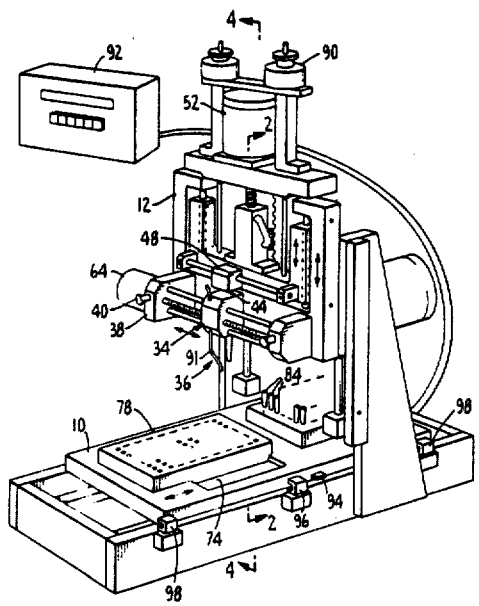

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-11 is confirmed.

* * * * *